United States Patent [19]

Nickell et al.

[11] Patent Number: 4,662,934

[45] Date of Patent: May 5, 1987

[54] METHOD OF INCREASING THE YIELD OF SUGAR FROM SUGARCANE

[75] Inventors: Louis G. Nickell, Chicago; Leonard J. Stach, Riverside; Takeo Hokama, Chicago, all of Ill.

[73] Assignee: Sandoz Ltd., Basel, Switzerland

[21] Appl. No.: 767,225

[22] Filed: Aug. 19, 1985

[51] Int. Cl.$^4$ ............................................. A01N 43/40
[52] U.S. Cl. ............................................. 71/94; 71/76
[58] Field of Search ..................................... 71/94, 76

[56] References Cited

U.S. PATENT DOCUMENTS

| | | | |
|---|---|---|---|
| 4,133,675 | 1/1979 | Schurter et al. | 71/94 |
| 4,233,054 | 11/1980 | Szczepanski et al. | 71/70 |
| 4,280,832 | 7/1981 | Koerwer | 71/94 |

*Primary Examiner*—Catherine L. Mills
*Attorney, Agent, or Firm*—Gerald D. Sharkin; Richard E. Vila

[57] ABSTRACT

The subject matter of this invention is the use of 2,4-dichlorophenoxyethyl 2-[4-(3,5-dichloropyridin-2-yloxy)phenoxy]propanoate as a sugarcane ripener.

9 Claims, No Drawings

METHOD OF INCREASING THE YIELD OF SUGAR FROM SUGARCANE

This invention relates to a method of increasing the yield of sugar obtained from sugarcane and more particularly relates to a method of increasing the recoverable sugar in sugarcane by treating the sugarcane plant during its maturation with 2,4-dichlorophenoxyethyl 2-[4-(3,5-dichloropyridin-2-yloxy)phenoxy]propanoate.

A variety of plant growth regulators, stimulants and promotors have been tried in the past in attempts to increase the yields of cultivated crops. It has been found that materials that have an effect on one crop will not necessarily have an effect or have a different effect on other crops.

One particular crop which has been given increased attention for the purpose of increasing yields is sugarcane. Accordingly it is an object of the present invention to provide new methods and compositions of increasing the yield of sugar obtained from sugarcane.

It has now been found that the recovery of sugar from sugarcane can be significantly increased by the use of certain esters. Consequently it has now been found that it is possible to increase the recoverable sugar in sugarcane by contacting the sugarcane plant with an effective amount of 2,4-dichlorophenoxyethyl 2-[4-(3,5-dichloropyridin-2-yl-oxy)phenoxy]propanoate.

The compound useful in the present method can be readily prepared by known esterification procedures. Thus the corresponding propionic acid chloride of the structured formula:

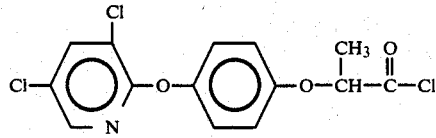

is reacted with 2,4-dichlorophenoxyethanol using standard esterification procedures i.e., heating in an inert solvent in the presence of an acid scavenger. The following example demonstrates the preparation of the desired propanoate ester.

EXAMPLE I

Preparation of 2,4-Dichlorophenoxyethyl 2-[4-(3,5-dichloropyridin-2-yl-oxy)phenoxy]propanoate 2-[4-(3,5-Dichloropyridin-2-yloxy)phenoxy]-propanoic acid (3.7 grams; 0.01128 mol) and thionyl chloride (15 ml) were placed into a 50 ml round bottomed glass reaction flask equipped with stirrer, condenser, thermometer and nitrogen line. This reaction mixture was stirred for 1¼ hours at 70° C. cooled and stripped yielding the desired acid chloride.

The 2-[4-(3,5-dichloropyridin-2-yloxy)phenoxy]-propanoic acid chloride (3.12 grams; 0.009 mol); triethylamine (5 ml); 2,4-dichlorophenoxyethethanol (1.94 grams; 0.0094 mol) and toluene (100 ml) were stirred in a glass reaction flask until thin layer chromatographic analysis showed completion of the reaction. This mixture was transferred to a separatory funnel and washed three times with water (70 ml). The washed material was dried and stripped to a yellow/brown gum (4.8 grams) that solidified on standing and was recrystallized from a mixture of methylene chloride and hexane. The first crop (1.5 grams) analyzed by elemental analysis as follows:

|    | Theoretical (%) | Found (%) |
|----|-----------------|-----------|
| C  | 51.09           | 51.36     |
| H  | 3.31            | 3.28      |
| N  | 2.71            | 2.76      |
| Cl | 27.42           | 27.26     |

It had a melting point of 100° C. and infrared analysis was consistent with the desired structure. A second crop (2.0 grams) was also obtained.

The effectiveness of the compounds of this invention for increasing the recoverable sugar from sugarcane was demonstrated in a field test by applying a solution in acetone diluted for application to sugarcane at the various indicated application rates. The test compound was applied at the test rate on the spindle area of each of 20 stalks of sugarcane in a field in Hawaii, using a syringe with a fine needle as the applicator. A set of 10 of these treated stalks from each group was harvested at 4 and 8 weeks after such treatment. In each harvest a set of 10 untreated stalks also harvested as a control.

The top 14 joints of the treated cane as well as those of the controls were removed, combined and analyzed for juice purity and pol percent cane, following the "press method" developed and described by T. Tanimoto, Hawaiian Planters Record, 57, 133 (1964). Pol percent cane is a polarimetric determination and equals the percentage of sucrose if the latter is the only substance in the solution which will rotate the plane of polarized light. The pol percent cane is a standard method of determining the sucrose content of sugarcane.

|                       | Rate Of Application (lbs. per acre) | Pol % Cane | Juice Purity |
|-----------------------|-------------------------------------|------------|--------------|
| Compound of Example 1 | 1.0                                 | 12.46      | 82.83        |
| Control               | 0                                   | 10.06      | 76.54        |

In the use of this compound to increase the recoverable sugar in sugarcane, sugarcane is treated at a late stage of development of the sugarcane wherein most of the sugar formation takes place. Thus, under normal growing conditions and common cultivation practices the active compound of this invention can be applied to the sugarcane during the period of from about 2 to about 10 weeks before harvesting.

The amount of active compound required to effectively increase the recoverable sugar from sugarcane can vary somewhat depending on such factors as the time of application, the weather, crop density, method of application and the like. Generally, an amount of at least 0.1 pounds per acre and preferably an amount of from 0.1 pounds per acre to about 10 pounds per acre can be used. While an amount greater than those mentioned can be used, they will not result in an advantage that would warrant their expense and are, therefore, not practical.

For practical use in treating sugarcane, the active compounds of this invention are generally incorporated into compositions or formulations which comprise an inert carrier and an effective amount of the compound. The compositions enable the active compound to be conveniently applied to the sugarcane at the desired rate. The formulations can be liquid formulations such as emulsifiable concentrates or solutions or solid formulations such as dusts, granules or wettable powders.

The preferred compositions are liquid formulations, particularly solutions or emulsifiable concentrates. Emulsifiable concentrates comprise the active compound, according to this invention, and as the inert carrier, a solvent and an emulsifier. Such emulsifiable concentrates can be extended with water and/or oil to any desired concentration of active compound for application as sprays to the sugarcane. The emulsifier most commonly used in these concentrates are nonionic or mixtures of nonionic with anionic surface-active agents. With the use of some emulsifier systems an inverted emulsion (water-in-oil) can be prepared.

Typical formulations according to the present invention useful for increasing the recoverable sugar in sugarcane are illustrated in the following examples wherein the quantities are given in parts by weight.

EXAMPLE 2

Preparation Of An Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

| | |
|---|---|
| Product of EXAMPLE 1 | 25 |
| Sodium lauryl sulfate | 2 |
| Sodium lignin sulfate | 3 |
| Kerosene | 70 |

EXAMPLE 3

Preparation Of A Wettable Powder

The following components are mixed intimately in conventional mixing or blending equipment and are then ground to a powder having a particle size of less than about 50 microns. The finished powder is dispersed in water to give the desired concentration of active compound for application to the sugarcane.

| | |
|---|---|
| Product of EXAMPLE 1 | 50 |
| Fuller's earth | 47 |
| Sodium lauryl sulfate | 2.5 |
| Methyl cellulose | 0.5 |

EXAMPLE 4

Preparation Of A Dust

The following ingredients are mixed thoroughly and are then ground to an average particle size of less than about 50 microns to give a dust suitable for application with conventional dusting equipment.

| | |
|---|---|
| Product of EXAMPLE 1 | 10 |
| Powdered talc | 90 |

What is claimed is:

1. A method for increasing the recoverable sugar contained in sugarcane which comprises contacting the sugarcane plant with an effective amount of 2,4-dichlorophenoxyethyl 2-[4-(3,5-dichloropyridin-2-yloxy)phenoxy]propanoate.

2. The method of claim 1 wherein the sugarcane is contacted with from about 0.1 to about 10 pounds per acre of the ester.

3. The method of claim 1 wherein the sugarcane is contacted with the ester during the period of from about 2 to about 10 weeks before harvest.

4. The method of claim 2 wherein the sugarcane is contacted with the ester during the period of from about 2 to about 10 weeks before harvest.

5. A method of claim 1 in which the ester is incorporated in a liquid composition.

6. A method of claim 5 in which the liquid composition is a solution.

7. A method of claim 5 in which the liquid composition is an emulsion.

8. A method of claim 7 in which a nonionic surface-active agent is present.

9. A method of claim 7 in which a mixture of nonionic and anionic surface-active agents are present.

* * * * *